United States Patent [19]
Grego et al.

[11] Patent Number: 5,644,391
[45] Date of Patent: Jul. 1, 1997

[54] METHOD OF AND DEVICE FOR DETERMINING THE POLYMERIZATION PROFILE OF A POLYMERIC LAYER

[75] Inventors: Giorgio Grego, S. Francesco Al Campo; Luigi Tallone, Paesana, both of Italy

[73] Assignee: Sip societa Italiana per l'Esercizio Delle Telecomunicazioni P.A., Turin, Israel

[21] Appl. No.: 619,425

[22] Filed: Mar. 21, 1996

[30] Foreign Application Priority Data

Mar. 22, 1995 [IT] Italy ................... TO95A0217

[51] Int. Cl.$^6$ ................... G01N 21/41
[52] U.S. Cl. ................... 356/128; 118/712
[58] Field of Search ................... 356/128, 73, 73.1, 356/319, 326; 118/688, 691, 712; 385/12

[56] References Cited

FOREIGN PATENT DOCUMENTS 1017978 5/1983 U.S.S.R. ................... 356/128

*Primary Examiner*—Hoa Q. Pham
*Attorney, Agent, or Firm*—Herbert Dubno

[57] ABSTRACT

To determine the polymerization profile of a layer of polymeric material, in particular a coating of an optical waveguide, a source sends a light radiation towards the layer under test at different angles of incidence, and both the portion of radiation reflected by the layer and the portion transmitted by the layer are converted into electrical signals. The electrical signals are supplied to devices for measuring their intensity, and a processing system processes the intensity values to obtain a value of the refractive index at a different depth inside the layer and to obtain the degree of polymerization at each depth by comparison with the values of the refractive index of a precursor of the polymer and of the fully polymerized material.

10 Claims, 3 Drawing Sheets

METHOD OF AND DEVICE FOR DETERMINING THE POLYMERIZATION PROFILE OF A POLYMERIC LAYER

FIELD OF THE INVENTION

The present invention related to the characterization of polymeric materials and, more particularly, to a method of and a device for determining the polymerization profile of one such material.

Preferably, but not exclusively, the invention can be applied to determination of the polymerization profiles of polymeric coatings of optical waveguides.

BACKGROUND OF THE INVENTION

It is well known that the degree of polymerization of a polymer determines many of its physical and mechanical characteristics, such as density, viscosity, refractive index, resistance to abrasion, response to tensile and flexure stresses, etc. When the polymer is used as a coating, for instance as a protective coating, the knowledge of those characteristics is also important for an understanding of the behavior of the coated body.

Considering the preferred application mentioned above, it is common practice to provide optical waveguides with a coating, generally made of an acrylate, intended to prevent chemical attack upon the waveguide and to improve its mechanical resistance to different kinds of stresses. It is essential that the characteristics of the coating remain constant in time, in order to guarantee a uniform behavior of the guides. Therefore it is also necessary, to this end, to monitor the degree of polymerization of the coating.

Devices for measuring the degree of polymerization of polymeric layers, in particular waveguide coatings polymerized by means of ultraviolet radiation, are commercially available. Such devices utilize infrared spectroscopy techniques and in particular exploit the fact that certain absorption peaks remain unchanged while others do change with the degree of polymerization. For example, in the case of an acrylate coating, use is made of the fact that the absorption peak of carbonyl group C=O is not influenced by polymerization, whereas the peak related to the double bond C=C of acrylate decreases as the degree of polymerization increases and becomes practically zero when polymerization is complete.

The known devices essentially are spectrometers equipped with an accessory allowing the analysis of multiple reflections within a crystal. For the measurement, first a sample of non-polymerised resin is applied onto the crystal, its infrared spectrum is determined and the ratio U between the areas of an absorption peak which is not affected by polymerization and of a peak that is affected by polymerization is computed. Subsequently, a sample of the coating under test is fixed to the crystal, infrared radiation is sent onto the sample at a pre-set angle such as to give rise to multiple reflections at the crystal-sample interface, and ratio BR between the areas of said peaks is computed both upon contact with the crystal surface bearing the sample that was directly exposed to a polymerizing radiation, and upon contact with the opposite surface. The relative variation (U-BR)/U of those ratios provides the degree of polymerization for the two faces of the coating. By using those devices it is possible to measure the degree of polymerization of coatings applied both to planar waveguides and to optical fibers.

The known devices, however, have the drawback of providing only information about the surfaces of the coating and not about its internal structure. Although the coatings of interest, particularly for the preferred application, have relatively limited thickness, there is no guarantee that information about the surface should also be valid for the mass of the polymer. Moreover, the measurement procedure is laborious, as it needs to be repeated for the two opposite surfaces of the material sample.

OBJECT OF THE INVENTION

It is an object of the invention to provide a method and a device which allow the polymerization profile of a coating (i.e. the behavior of the degree of polymerization throughout the entire thickness of the coating) to be determined in a single operation.

SUMMARY OF THE INVENTION

According to the method, light radiation is sent towards the layer under test at different angles of incidence. Both the portion of the radiation reflected by the layer and the portion transmitted are transformed into electrical signals. The intensities of the electrical signals are measured; the values of the reflectance and transmittance of the layer are obtained from the resulting values of intensity. A value of the refractive index at a different depth inside the layer is obtained from the values of reflectance and transmittance relevant to each angle of incidence; and the degree of polymerization at each depth is obtained by comparison with the values, determined in a calibration phase, of the refractive index of a precursor of the polymer and of the fully polymerized material.

The device comprises: a light radiation source; means for sending that radiation towards a layer under test, at different angles of incidence; means for collecting and converting into electrical signals both the portion of radiation transmitted by the layer and the portion reflected by the layer; means for measuring the intensity of these electrical signals; and a processing system arranged to: obtain the transmittance and reflectance of the layer at the different angles of incidence from the values of intensity, obtain a value of the refractive index at a different depth inside the layer from the values of reflectance and transmittance relevant to each angle of incidence; and obtain the degree of polymerisation at each depth by comparison with the values, determined in a calibration phase and stored in the processing system, of the refractive index of a precursor of the polymer and of the fully polymerized polymeric material.

BRIEF DESCRIPTION OF THE DRAWING

The above and other objects, features, and advantages will become more readily apparent from the following description, reference being made to the accompanying drawing in which.

Figure 1:
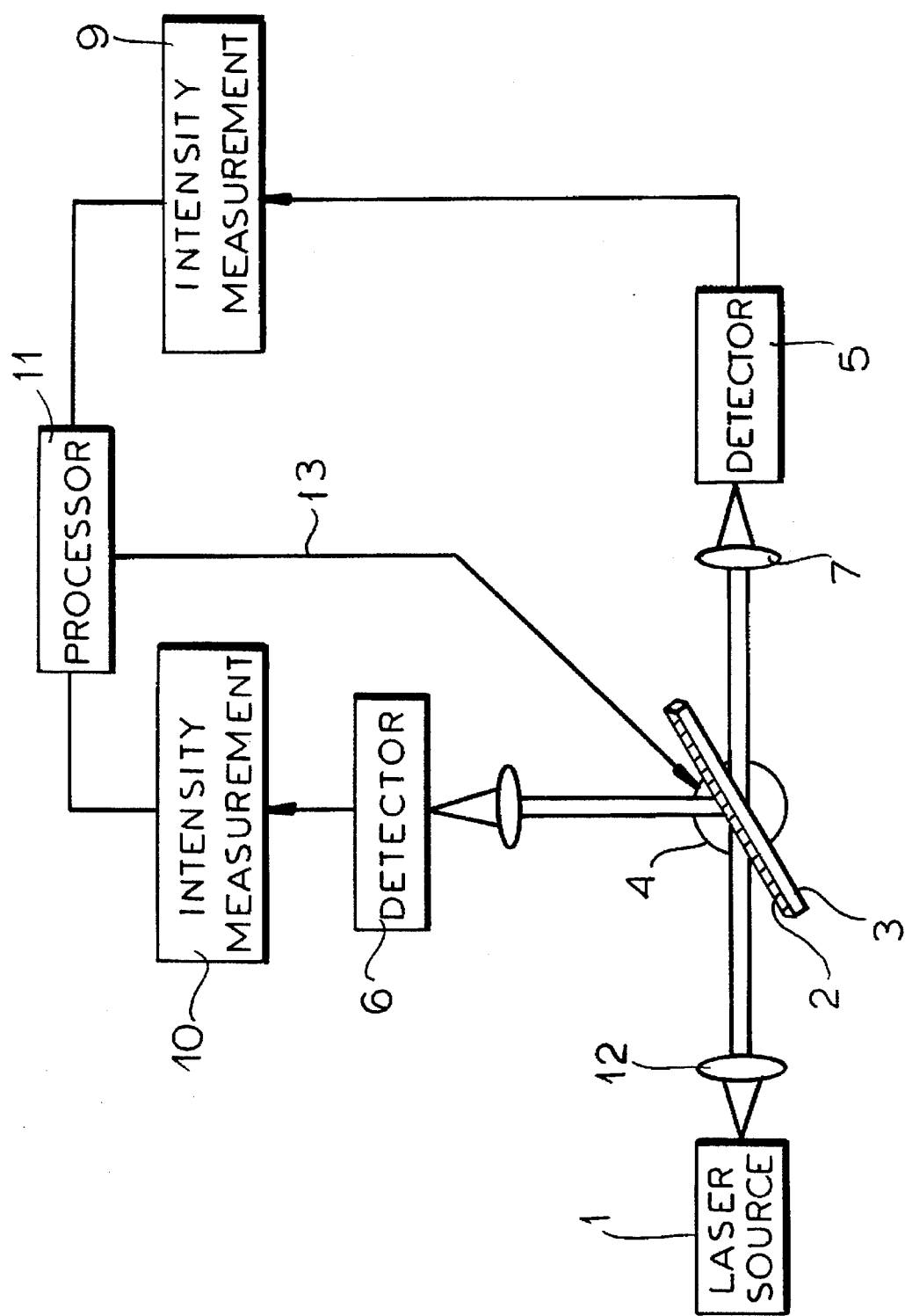
FIGS. 1 and 2 all block diagrams which show two possible embodiments of the invention for determining the polymerization profile of the coating of a planar optical waveguide.

In the drawings, thick lines indicate electrical connections.

In FIG. 1, the light emitted by a source 1, for instance a laser, is sent onto a sample 2 of the polymer to be analyzed, possibly through an optical collimating system, represented schematically by lens 12. The sample is a very thin layer (e.g. 50 μm thick) applied on a glass plate 3. The sample is borne by a support, indicated schematically as 4, which allows the sample orientation with respect to the incident beam to be varied. The radiation transmitted and the radiation reflected by sample 2 are focused on detectors 5, 6, respectively, by means of optical systems represented schematically by lenses 7, 8. The electrical signals generated by detectors 5, 6 are supplied to intensity measuring devices 9, 10, which supply a processor 11 with the measured values of intensity. Advantageously the processor also controls the support rotation, as depicted schematically by connection 13. The processor is arranged to: establish an association between the intensity information provided by detectors 5, 6 to the angle of incidence of the beam emitted by source 1; determine the values of reflectance and transmittance as the angle varies, starting from the intensity information; and obtain the polymerization profile of the sample from the reflectance and transmittance values.

Figure 2:
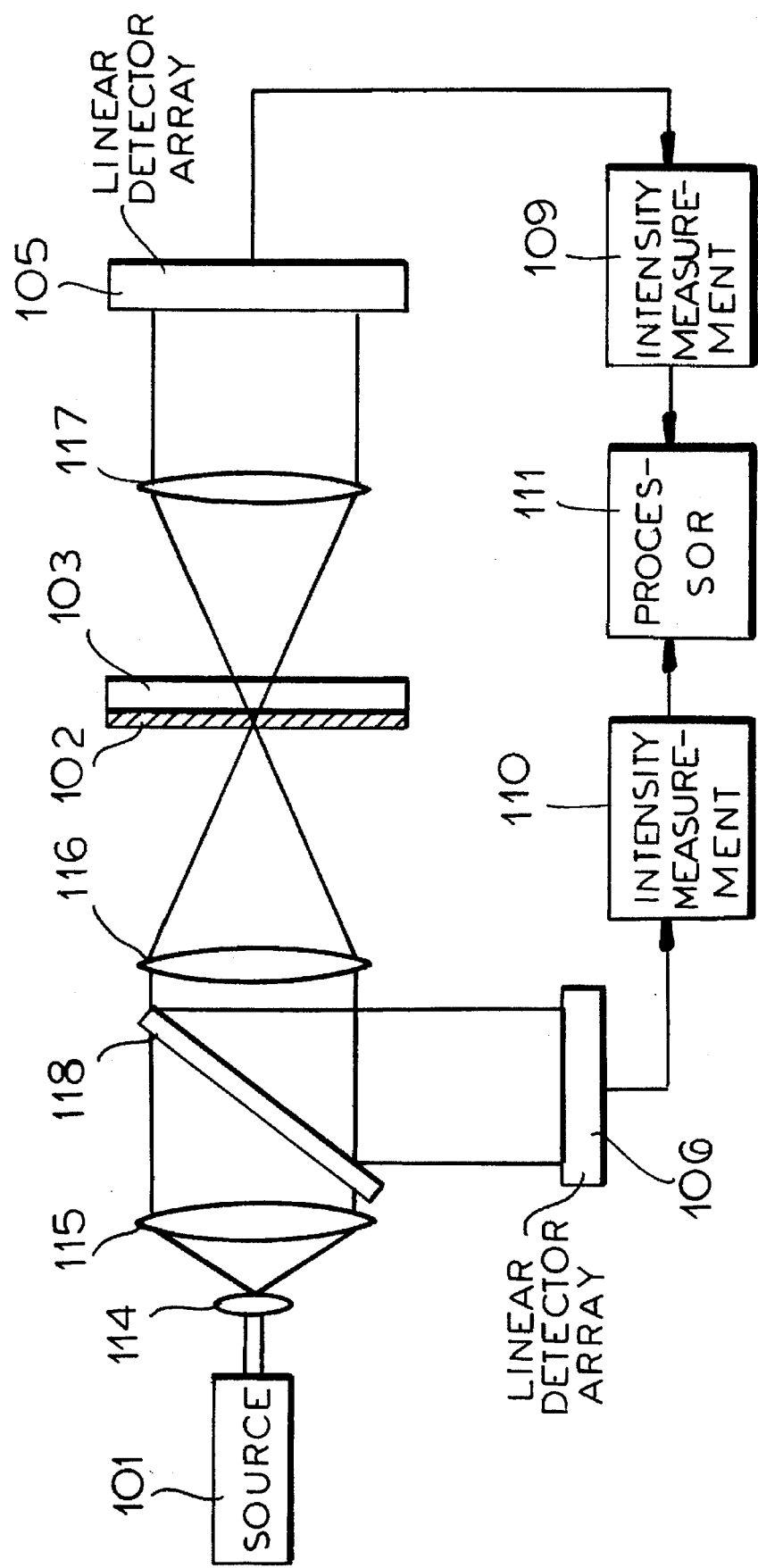

In FIG. 2, the light emitted by source 101 is sent onto sample 102, mounted on plate 103, through an optical focusing system schematically represented by lenses 114, 115, 116. Through an optical collimating system schematically represented by lens 117, the light transmitted by sample 102 is collimated onto a linear detector array 105, where each detector receives the light refracted by sample 102 inside a certain range of angles. The light reflected by sample 102 is collected by lens 116 and collimated onto a semitransparent mirror 118, which is placed between lenses 115 and 116 and on one side transmits the light coming from source 101 towards lens 116 and sample 102, and on the other side reflects the light reflected by sample 102 towards a linear detector array 106, analogous to array 105. Like the detectors in array 105, each detector in array 106 receives the radiation reflected by the sample within a certain range of angles. It is evident that the optical systems which allow the radiation transmitted or reflected by the sample to be transferred to the respective detectors must ensure a one-to-one correspondence between the detectors in both arrays. The detectors in arrays 105, 106 are connected to respective intensity measuring devices 109, 110, which in turn supply processor 111 with intensity information. As before, the processor establishes an association between the signals provided by the detectors and the angle of incidence, and then the polymerization profile can be obtained starting from the measure of reflectance and transmittance as a function of the angle of incidence.

Figures 3, 4:
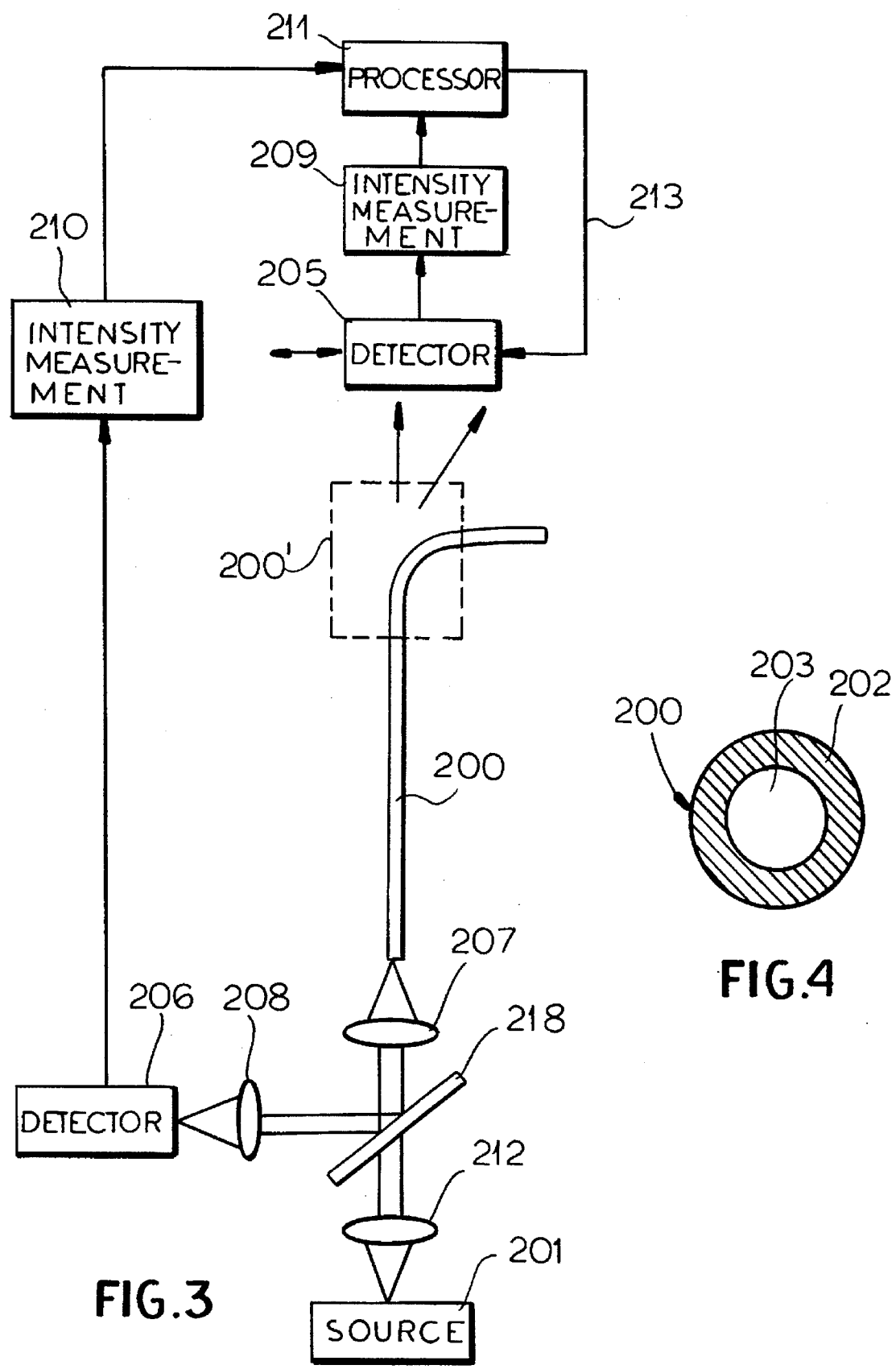
FIG. 3 is a block diagram which shows an embodiment of the invention that is suitable for the determination of the polymerization profile of the coating of an optical fiber.
FIG. 4 is a cross section of the fiber.

With reference to FIGS. 3 and 4, source 201 launches light radiation into a length of coated optical fiber 200 through an optical system schematically represented by lenses 212, 207. Reference numeral 202 indicates the polymeric coating and 203 the glass part (i.e. the bare fiber). Coated fiber 200 is mounted on a support (not shown) which is so constructed that the fiber presents a curved region 200' with variable radius of curvature. In that region, the radiation guided in the fiber reaches the interface between glass part 203 and coating 202 with a variable angle of incidence, and a fraction of the radiation will exit through coating 202. That fraction is collected by a detector 205 which is placed on a support (incorporated in the detector itself to keep the drawing simple) which can be displaced parallel to itself in order to collect rays exiting different points of fiber region 200'. The displacements of the detector can be controlled by processor 211, as schematically shown by connection 213. As in the previous embodiments, detector 205 is associated with a device 209 measuring the intensity of the electrical signal generated by the detector itself, which device is connected to processor 211 associating intensity information with the position of the detector, and therefore with the angle of incidence of the radiation guided in the fiber on the glass-coating interface. A semi-transparent mirror 218 located between lenses 212 and 207 collects the radiation backscattered in the fiber and sends it, through an optical system 208, to a detector 206 associated with a device 210 measuring the intensity of the signals emitted by the detector. Measuring device 210 is a part, together with source 201, of a time domain reflectometry system which allows information on the intensity of the radiation backscattered to be associated with information on the point from which the radiation originated and therefore with the angle of incidence on the glass-coating interface. Also measuring device 210 is connected to processor 211 which, as in the previous embodiments, can determine transmittance and reflectance as a function of the angle of incidence and thus obtain the polymerization profile.

In order to determine reflectance and transmittance at different depths inside the polymeric sample, the latter can for instance be assimilated to a multi-layer structure in which the generic layer j has a complex refractive index $\tilde{n}_j = n_j + ik_j$, where k is the absorption of the material. Reflectance and transmittance at the different angles of incidence are linked to the values of n and k by relations reported for instance in the paper "Optimization of optical parameters and electric field distribution in multilayers", by F. Demichelis et al., Applied Optics, Vol. 23, No. 1, 1 Jan. 1984.

Those relations are obtained starting from the assumption that, in each layer, the electromagnetic field consists of two plane waves propagating in opposite directions. Each wave is characterized by a complex constant which defines its intensity and its phase. Taking into account that only the wave which propagates in the positive direction (i.e. in the same direction as the radiation emitted by the source) exists beyond the multi-layer (i.e. in plate 3, considering for the sake of simplicity the case of the plane layer) and imposing the continuity of the components of the electrical and magnetic fields which are parallel to the separation surfaces between the layers, it is possible to obtain recursive relations by which the constants of the incident wave and of the reflected wave immediately before the first layer can be computed. The reflectance of the multi-layer can easily be determined from these constants. Transmittance in turn is linked to the values of the constants beyond the last layer. Since, as stated above, for each angle of incidence and for each layer transmittance and reflectance are known functions of n and k, by applying the relations reported in the article the processing system can immediately determine, for instance with the least squares method, the combination of pairs of values n, k which best fits the experimental data obtained for reflectance and transmittance. Once this combination of value pairs has been determined, the degree of polymerization of the individual layer will be obtained by comparison with the corresponding values of n, k for the non-polymerized liquid and for the fully polymerized material.

Therefore, to perform the method according to the invention, it will be necessary to determine, in a calibration phase, the profile of the complex refractive index for a layer, of the same thickness as the sample, of the polymer precursor liquid and for a fully polymerized layer. This calibration phase can be carried out once and for all for a given coating material, or it can be repeated each time. Subsequently, the actual measurement will be carded out on the sample under test.

It is preferable to use, for the measurement, a radiation whose wavelength corresponds to an absorption peak of the material under test. In this case, refractive index variation, which is mainly due to the variation of k, is particularly marked.

Obviously, different computational methods can be used to determine n and k starting from the reflectance and transmittance values. An alternative method is described by P. H. Berning in "Theory and calculation of optical thin films", Physics of Thin Films, Vol. 1, pp. 69 et seq.

Moreover, although the above description refers in particular to the determination of the polymerization profile of a coating of a planar optical waveguide or of an optical fiber, the invention can be used to determine the polymerisation profile of any polymeric layer, provided its width is sufficient to allow illumination with the beam emitted by the source.

We claim:

1. A method of determining a polymerization profile of a layer of polymeric material comprising the steps of:
   (a) sending a light radiation towards a layer of polymeric material under test at different angles of incidence;
   (b) transforming both a portion of radiation reflected by the layer and a portion of radiation transmitted by the layer into respective electrical signals;
   (c) measuring the intensity of each of said electrical signals as the angle of incidence varies and obtaining values of reflectance and transmittance of the layer relevant to different angles of incidence are obtained from said measurements of intensity;
   (c) obtaining a value of refractive index at a different depth inside the layer from said values of reflectance and transmittance relevant to each angle of incidence; and
   (e) obtaining a degree of polymerization at each depth by comparison of said refractive index with refractive indexes determined in a calibration phase of a precursor of the polymer and of the fully polymerized material.

2. The method defined in claim 1 wherein said light radiation has a wavelength corresponding to an absorption peak of the material of the layer.

3. The method defined in claim 1 wherein said layer is a polymeric coating of an optical waveguide.

4. The method defined in claim 3 wherein said polymeric coating is a coating of a planar optical waveguide; and wherein for the measurement, a sample of the coating is applied onto a transparent plate, and the different angles of incidence are obtained selectively by one of the steps of making the plate rotate with respect to a collimated beam of the radiation and by focusing the radiation onto the plate which is kept stationary.

5. The method defined in claim 3 wherein said polymeric coating is a coating applied onto an optical fiber into which a collimated beam of the radiation emitted by a source is sent, and wherein the coated fiber comprises a curved region with a variable radius of curvature, so that in said curved region said beam reaches an interface between the fiber and the coating at different angles of incidence, such that a portion of the beam exits through the coating to form the transmitted radiation and a portion is backscattered to form the reflected radiation.

6. A device for determining a polymerization profile of a layer of polymeric material, said device comprising:
   a light radiation source;
   means for sending light radiation from said source towards a polymeric layer under test at different angles of incidence;
   means for collecting and converting into electrical signals both a portion of radiation transmitted by the layer and a portion reflected by the layer;
   means for measuring the intensity of said electrical signals; and
   a processing system arranged to obtain values of a transmittance of a reflectance of the layer at the different angles of incidence from measured values of intensity, obtain a value of the refractive index at a different depth inside the layer from the values of reflectance and transmittance relevant to each angle of incidence, and obtain a degree of polymerization at each depth by comparison with the values, determined in a calibration phase and stored in the processing system, of the refractive index of a precursor of the polymer and of the fully polymerized polymeric material.

7. The device defined in claim 6 wherein said layer is a polymeric coating of a planar optical waveguide, and the device further comprises a transparent support plate for supporting a sample of the coating, and said means for sending the radiation towards the sample at different angles comprises a support on which the plate is mounted and which is arranged to vary the inclination of the plate under the control of the processing system with respect to a collimated beam of the radiation.

8. The device defined in claim 6 wherein said layer is a polymeric coating of a planar optical waveguide, and in that the device further comprises a transparent support plate for a sample of the coating, said means for sending the radiation towards the sample at different angles comprising an optical system focusing the radiation onto the sample.

9. The device defined in claim 6 wherein said layer is a layer of a coating of an optical fiber into which the light radiation source sends a collimated radiation beam and which has a region with variable curvature, so that the radiation sent into the fiber arrives at different angles of incidence at different points of an interface separating the glass portion from the coating of the fiber, said means for collecting and converting into electrical signals the transmitted and reflected radiation portion being arranged to collect and convert into electrical signals respectively a portion of radiation which is not guided and exits the fiber through the coating in said region and the radiation backscattered from points of said region.

10. The device defined in claim 9 wherein said means for collecting and converting into electrical signals the transmitted radiation comprises a detector which is displaced parallel to itself, along a trajectory encompassing the whole angle of aperture of the radiation portion exiting from the variable curvature region of the fiber, under the control of the processing system, so that each information about the intensity provided by the means for measuring the intensity of the transmitted radiation can be associated with a portion of a respective detector and therefore with an angle of incidence, said means for collecting and converting into electrical signals the reflected radiation comprising a detector which is associated with the intensity measuring means and is part together with the source of a time domain reflectometry system arranged to associate the information on the intensity of the backscattered radiation with the point of said variable curvature region in which backscattering occurred, and therefore with an angle of incidence.

* * * * *